US00PP19339P2

(12) United States Plant Patent
Bernuetz

(10) Patent No.: US PP19,339 P2
(45) Date of Patent: Oct. 14, 2008

(54) ***ARGYRANTHEMUM* PLANT NAMED 'OHMADPORM'**

(50) Latin Name: *Argyranthemum×hybrida*
Varietal Denomination: Ohmadporm

(75) Inventor: Andrew Bernuetz, Silverdale (AU)

(73) Assignee: Bonza Botanicals Pty. Ltd., Yellow Rock, NSW (AU)

( * ) Notice: Subject to any disclaimer, the term of this patent is extended or adjusted under 35 U.S.C. 154(b) by 0 days.

(21) Appl. No.: 11/700,678

(22) Filed: Jan. 30, 2007

(51) Int. Cl.
*A01H 5/00* (2006.01)

(52) U.S. Cl. ..... Plt./263.1

(58) Field of Classification Search ..... Plt./263
See application file for complete search history.

(56) References Cited

PUBLICATIONS

PBR 20041919 filed Oct. 25, 2004.*

* cited by examiner

*Primary Examiner*—Kent L. Bell
*Assistant Examiner*—Georgia Helmer
(74) *Attorney, Agent, or Firm*—C. A. Whealy

(57) ABSTRACT

A new and distinct cultivar of *Argyranthemum* plant named 'Ohmadporm', characterized by its compact, uniform and mounded plant habit; freely branching and vigorous growth habit; freely flowering habit; semi-double type inflorescences with red purple-colored ray florets; and good garden performance.

1 Drawing Sheet

Botanical designation: *Argyranthemum×hybrida*.
Cultivar denomination: 'OHMADPORM'.

BACKGROUND OF THE INVENTION

The present invention relates to a new and distinct cultivar of *Argyranthemum* plant, botanically known as *Argyranthemum×hybrida* and hereinafter referred to by the name 'Ohmadporm'.

The objective of the breeding program is to create new *Argyranthemum* cultivars with numerous inflorescences, attractive floret colors, and good garden performance.

The new *Argyranthemum* originated from a cross-pollination made by the Inventor in 2001 in Winmalee, New South Wales, Australia of a proprietary selection of *Argyranthemum×hybrida* identified as code number 01-233, not patented, as the female, or seed, parent with a proprietary selection of *Argyranthemum×hybrida* identified as code number 01-235, as the male, or pollen, parent. The new *Argyranthemum* was discovered and selected by the Inventor as a single flowering plant within the progeny of the stated open-pollination in a controlled environment in Winmalee, New South Wales, Australia.

Asexual reproduction of the new *Argyranthemum* by vegetative tip cuttings was first conducted in Winmalee, New South Wales, Australia in September, 2003. Asexual reproduction by cuttings has shown that the unique features of this new *Argyranthemum* are stable and reproduced true to type in successive generations.

SUMMARY OF THE INVENTION

Plants of the cultivar Ohmadporm have not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Ohmadporm'. These characteristics in combination distinguish 'Ohmadporm' as a new and distinct potted *Argyranthemum* cultivar.

1. Compact, uniform and mounded plant habit.
2. Freely branching and vigorous growth habit.
3. Freely flowering habit.
4. Semi-double type inflorescences with red purple-colored ray florets.
5. Good garden performance.

Plants of the new *Argyranthemum* differ from plants of the female parent selection in the following characteristics:

1. Plants of the new *Argyranthemum* have smaller leaves than plants of the female parent selection.
2. Plants of the new *Argyranthemum* have semi-double type inflorescences whereas plants of the female parent selection have single inflorescences.
3. Plants of the new *Argyranthemum* and the female parent selection differ in ray floret color as plants of the female parent selection have yellow-colored ray florets.

Plants of the new *Argyranthemum* differ from plants of the male parent selection in the following characteristics:

1. Plants of the new *Argyranthemum* have semi-double type inflorescences whereas plants of the male parent selection have single inflorescences.
2. Plants of the new *Argyranthemum* and the male parent selection differ in ray floret color as plants of the male parent selection have yellow-colored ray florets.

Plants of the new *Argyranthemum* can be compared to plants of the *Argyranthemum* cultivar Ohmadsavi, disclosed in U.S. Plant Pat. No. 16,648. In side-by-side comparisons conducted in Winmalee, New South Wales, Australia, plants of the new *Argyranthemum* differed from plants of the cultivar Ohmadsavi in the following characteristics:

1. Plants of the new *Argyranthemum* were more compact than plants of the cultivar Ohmadsavi.
2. Plants of the new *Argyranthemum* were more freely branching than plants of the cultivar Ohmadsavi.
3. Plants of the new *Argyranthemum* had smaller leaves than plants of the cultivar Ohmadsavi.
4. Inflorescences of plants of the new *Argyranthemum* had more ray florets, but fewer disc florets than inflorescences of plants of the cultivar Ohmadsavi.
5. Plants of the new *Argyranthemum* and the cultivar Ohmadsavi differed in ray floret coloration.

BRIEF DESCRIPTION OF THE PHOTOGRAPHS

The accompanying photographs illustrate the overall appearance of the new *Argyranthemum.* These photographs show the colors as true as it is reasonably possible to obtain in colored reproductions of this type. Colors in the photographs may differ slightly from the color values cited in the detailed botanical description which accurately describe the colors of the new *Argyranthemum.*

The photograph at the top of the sheet comprises a side perspective view of a typical flowering plant of 'Ohmadporm' grown in a container.

The photograph at the bottom of the sheet is a close-up view of the typical inflorescences of 'Ohmadorm'.

DETAILED BOTANICAL DESCRIPTION

The aforementioned photographs and following observations and measurements describe plants grown during the summer and autumn in Higashiomi, Shiga, Japan in a greenhouse and under conditions and practices which approximate those generally used in commercial potted *Argyranthemum* production. During the production of the plants, day temperatures ranged from 25° C. to 30° C. and night temperatures ranged from 15° C. to 20° C. Plants were pinched one time. Plants used in the photographs and for the description were about three months old. In the following description, color references are made to The Royal Horticultural Society Colour Chart, 2001 Edition, except where general terms of ordinary dictionary significance are used.

Botanical classification: *Argyranthemum×hybrida* cultivar Ohmadporm.

Parentage:

*Female, or seed, parent.*—Proprietary selection of *Argyranthemum×hybrida* identified as code number 01-233, not patented.

*Male, or pollen, parent.*—Proprietary selection of *Argyranthemum×hybrida* identified as code number 01-235, not patented.

Propagation:

*Type.*—Terminal cuttings.

*Time to initiate roots.*—About six to eight days at temperatures of about 20° C. to 25° C.

*Time to produce a rooted young plant.*—About three to four weeks at temperatures of about 20° C. to 25° C.

*Root description.*—Fine, fibrous.

*Rooting habit.*—Freely branching.

Plant description:

*Appearance.*—Herbaceous semi-double type potted *Argyranthemum.* Compact, uniform and mounded plant habit. Strong and freely branching growth habit with about 20 lateral branches developing per plant; dense and full plants. Vigorous growth habit.

*Plant height.*—About 23.3 cm.

*Plant width.*—About 19.3 cm.

*Lateral branches.*—Length: About 11.2 cm. Diameter: About 3 mm. Internode length: About 5 mm. Strength: Strong; young stems, flexible. Texture: Smooth, glabrous. Color: 144C.

Foliage description:

*Arrangement.*—Alternate, simple.

*Length.*—About 5.2 cm.

*Width.*—About 2.4 cm.

*Apex.*—Acute.

*Base.*—Attenuate.

*Margin.*—Pinnatifid.

*Texture, upper and lower surfaces.*—Smooth, glabrous.

*Venation.*—Pinnate, reticulate.

*Color.*—Developing foliage, upper surface: 144A. Developing foliage, lower surface: 137C. Fully expanded foliage, upper surface: 137A; venation, 145A. Fully expanded foliage, lower surface: 137C; venation, 145A.

*Petiole.*—Length: About 1.5 cm. Diameter: About 0.7 mm. Texture, upper and lower surface: Sparsely pubescent. Color, upper and lower surfaces: 145A.

Inflorescence description:

*Appearance.*—Semi-double type inflorescence form with elliptic-shaped ray florets. Inflorescences borne on terminals above foliage. Disc and ray florets arranged acropetally on a capitulum. Inflorescences slightly fragrant.

*Flowering season.*—Plants flower from spring to early fall in Japan; flowering continuous during this period.

*Inflorescence longevity.*—Inflorescences last about seven to ten days on the plant; inflorescences persistent.

*Quantity of inflorescences.*—Freely flowering, about three to four open inflorescences per lateral branch at one time.

*Inflorescence bud.*—Height: About 6 mm. Diameter: About 5 mm. Shape: Ovoid. Color: 162D.

*Inflorescence size.*—Diameter: About 4.1 cm. Depth (height): About 1.9 cm. Diameter of disc: About 1.5 cm.

*Ray florets.*—Shape: Elliptic. Length: About 1.5 cm. Width: About 3.3 mm. Apex: Emarginate, praemorse. Base: Obtuse. Margin: Entire. Texture, upper and lower surfaces: Smooth, glabrous. Number of ray florets per inflorescence: About 120 arranged in several imbricate whorls. Color: When opening, upper surface: 64B. When opening, lower surface: N74C. Fully opened, upper surface: N74D; color becoming closer to 75D with development. Fully opened, lower surface: 75C.

*Disc florets.*—Arrangement: Massed at center of receptacle. Shape: Tubular, elongated. Apex: Five-pointed. Length: About 5 mm. Diameter: About 1 mm. Number of disc florets per inflorescence: About 50. Color, immature: 154C. Color, mature: 12A.

*Phyllaries.*—Number of phyllaries per inflorescence: About 20. Length: About 3 mm. Width: About 2 mm. Shape: Elliptic. Apex: Acute. Base: Truncate. Margin: Entire. Texture, upper and lower surfaces: Smooth, glabrous; margins, papery. Color, upper and lower surfaces: 144C.

*Peduncles.*—Length: About 12.8 cm. Diameter: About 1 cm. Angle: Mostly erect. Strength: Strong, flexible. Texture: Smooth, glabrous. Color: 144A.

*Reproductive organs.*—Androecium: Present on disc florets only. Anther length: About 1 mm. Anther shape: Ellipsoidal. Anther color: 34B. Pollen amount: Scarce.

*Gynoecium.*—Present on both ray and disc florets. Pistil length: About 3 mm. Stigma shape: Two-parted. Stigma color: 17B. Ovary color: 145D.

*Seed/fruit.*—Seed and fruit production has not been observed.

Disease/pest resistance: Resistance to pathogens and pests common to *Argyranthemums* has not been observed on plants grown under commercial conditions.

Garden performance: Plants of the new *Argyranthemum* have been observed to have good garden performance and to tolerate wind, rain and temperatures from about 0° C. to about 40° C.

It is claimed:

1. A new and distinct *Argyranthemum* plant named 'Ohmadporm' as illustrated and described.

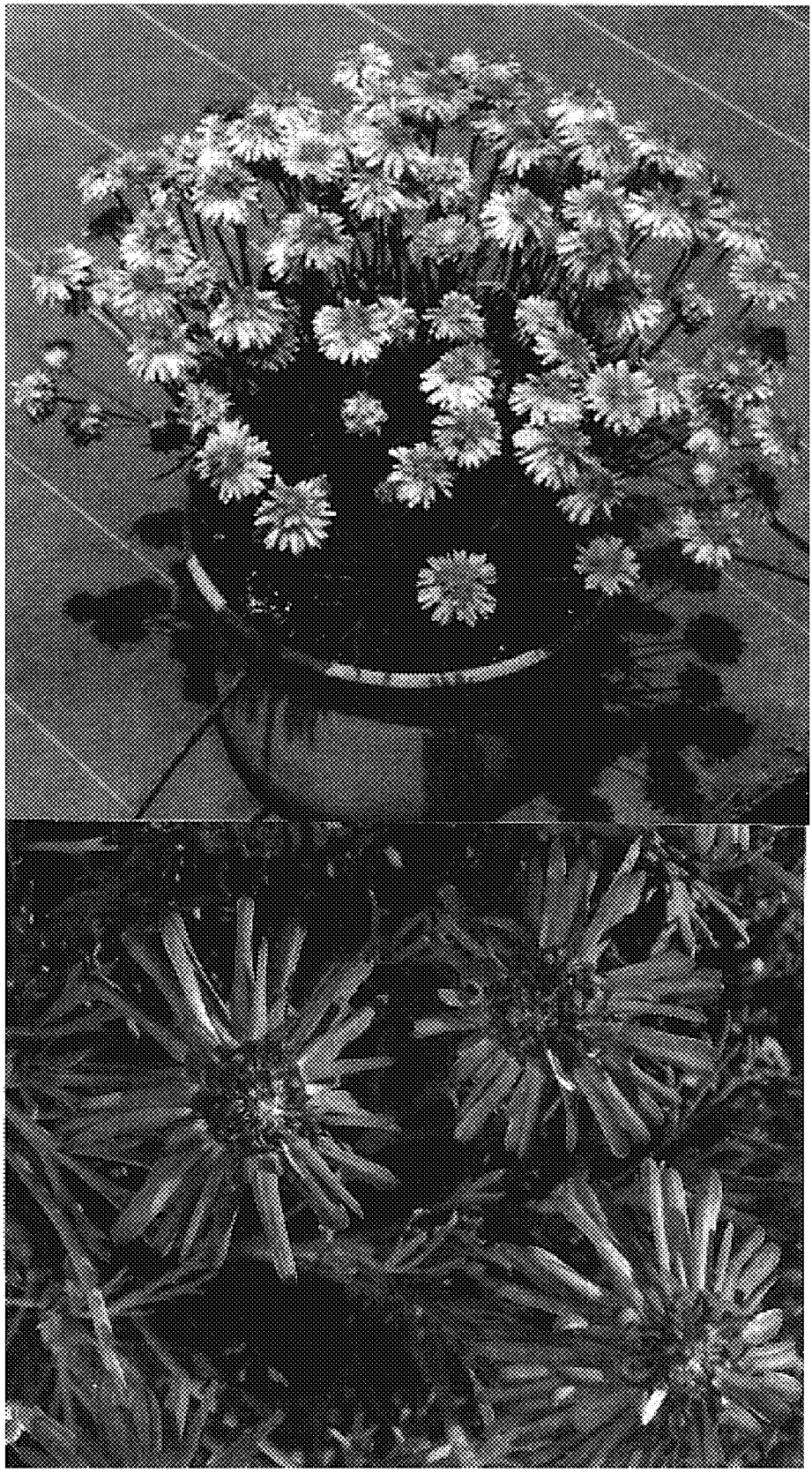

* * * * *